US009606093B2

(12) United States Patent
Alquaity et al.

(10) Patent No.: US 9,606,093 B2
(45) Date of Patent: Mar. 28, 2017

(54) CAVITY RING-DOWN SPECTROSCOPIC SYSTEM AND METHOD

(71) Applicants: Awad Bin Saud Alquaity, Thuwal (SA); Aamir Farooq, Thuwal (SA)

(72) Inventors: Awad Bin Saud Alquaity, Thuwal (SA); Aamir Farooq, Thuwal (SA)

(73) Assignee: KING OF ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 14/540,410

(22) Filed: Nov. 13, 2014

(65) Prior Publication Data

US 2015/0131094 A1     May 14, 2015

Related U.S. Application Data

(60) Provisional application No. 61/903,640, filed on Nov. 13, 2013.

(51) Int. Cl.
| | | |
|---|---|---|
| *G01N 21/00* | (2006.01) | |
| *G01N 33/00* | (2006.01) | |
| *G01J 3/42* | (2006.01) | |
| *G01N 21/39* | (2006.01) | |
| *G01N 21/03* | (2006.01) | |

(52) U.S. Cl.
CPC ............ G01N 33/0027 (2013.01); G01J 3/42 (2013.01); G01N 21/39 (2013.01); *G01N 21/031* (2013.01); *G01N 2021/396* (2013.01); *G01N 2201/0697* (2013.01)

(58) Field of Classification Search
CPC .... G01N 21/39; G01N 21/031; G01N 21/552; G01N 15/1459; G01N 2015/1493; G01N 2021/0193; G01N 2021/391; G01N 21/01; G01N 21/3504; G01N 21/49; G01N 21/70; G01N 21/7703; G01N 2291/0427; G01N 33/01
See application file for complete search history.

(56) References Cited

U.S. PATENT DOCUMENTS

| | | | | |
|---|---|---|---|---|
| 5,903,358 A * | 5/1999 | Zare | ................. | G01J 3/10 250/343 |
| 6,466,322 B1 * | 10/2002 | Paldus | ................. | G01N 21/39 356/437 |
| 7,323,677 B1 * | 1/2008 | Wang | ................. | G01J 5/08 250/227.14 |
| 8,149,407 B1 * | 4/2012 | Rao | ................. | G02B 5/003 356/437 |
| 8,642,982 B2 * | 2/2014 | Plusquellic | ............ | G01J 3/108 250/351 |
| 2008/0218736 A1 * | 9/2008 | Shaw | ................. | G01N 21/553 356/72 |

* cited by examiner

*Primary Examiner* — Michael P Stafira
(74) *Attorney, Agent, or Firm* — Patent Portfolio Builders PLLC

(57) ABSTRACT

A system and method for cavity ring-down spectroscopy can include a pulsed quantum cascade laser, an optical ring-down cavity, a photodetector, and an oscilloscope. The system and method can produce pulse widths of less than 200 ns with bandwidths greater than 300 pm, as well as provide temporal resolution of greater than 10 μs.

22 Claims, 8 Drawing Sheets

CAVITY RING-DOWN SPECTROSCOPIC SYSTEM AND METHOD

CLAIM OF PRIORITY

This application claims priority from U.S. Provisional Patent Application No. 61/903,640, filed Nov. 13, 2013, which is incorporated by reference in its entirety.

TECHNICAL FIELD

The present invention is directed to a system and method for absorption spectroscopy and, in particular, for measuring constituents of gas in a ring-down spectrometer.

BACKGROUND

Absorption spectroscopy has long been used for detecting the composition of matter and measuring trace constituents of matter. For example, photoacoustic spectroscopy can be used for ammonia detection. In an exemplary spectrometer, a $CO_2$ laser with a resonant photoacoustic cell can be used to achieve a detection limit of 0.1 ppb for ammonia. Sensors have also been developed for ammonia detection in semiconductor industry as well as for atmospheric pollution monitoring. Somewhat relatedly, intra and inter pulse techniques with a long path length Herriot cell can be used to achieve ppb-level of detection of, for example, acrolein and acrylonitrile with a total integration time of approximately 10 seconds. A sensor can also be developed based on direct absorption in a multi-pass Herriot cell to monitor ethylene concentrations in vehicle exhaust and in air sampled from high-traffic urban tunnel.

Cavity ring-down spectroscopy (CRDS) is a form of absorption spectroscopy. CRDS utilizes the mean lifetime of photons in a high-finesse optical resonator with an absorbing medium present in the cavity. CRDS can excel in the low-absorbance regime where conventional methods have inadequate sensitivity.

SUMMARY

In an aspect, a ring-down spectrometer can include a pulsed quantum cascade laser configured to produce a laser beam, an optical ring-down cavity, a photodetector, and an oscilloscope. The laser beam can be arranged to propagate through the optical cavity. The photodetector can be configured to receive the laser beam and produce signals. The oscilloscope can be configured to receive the signals.

In some embodiments, the pulsed quantum cascade laser can be an external cavity laser having a laser controller. The optical ring-down cavity can have at least one mirror having a reflectivity of 99.5 percent or more.

In other embodiments, the ring-down spectrometer can include a spectral analyzer. The laser controller can be configured to tune the quantum cascade laser based on an output from the spectrum analyzer.

In yet other embodiments, the quantum cascade laser is configured to provide a single mode laser beam. The laser beam can have pulses having pulse widths of less than 1 microsecond, less than 300 nanoseconds, and/or less than 100 nanoseconds. Each of the pulses can have a bandwidth greater than 500 picometers, greater than 900 picometers, greater than 1000 picometers or wider. The photodetector and the oscilloscope can be configured to provide a temporal resolution of greater than 100 microseconds, greater than 10 microseconds, greater than 100 nanoseconds.

In another aspect, a ring-down spectroscopic method can include producing laser pulses, propagating the laser pulses through an optical ring-down cavity, detecting ring-down pulses, and analyzing the ring-down pulses to determine an absorption coefficient based on a ring-down time. Each of the pulses can have a pulse width of less than 1 microsecond, less than 500 nanosecond, less than 300 nanoseconds. Each of the pulses can have a bandwidth greater than 500 picometers, greater than 900 picometers, greater than 1000 picometers or wider. The optical ring-down cavity can have at least one partially reflecting mirror to produce ring-down pulses.

In some embodiments, producing the laser pulses can include varying the pulse width to identify an optimum value.

In other embodiments, the pulse width can be less than 1 microsecond, less than 300 nanoseconds, and/or less than 100 nanoseconds. The laser pulses can have a bandwidth greater than 500 picometers, greater than 900 picometers, greater than 1000 picometers or wider, and/or wider bandwidths.

In yet other embodiments, analyzing the ring-down pulses can include a step of removing noise. The step of removing noise can include averaging a plurality of the ring-down pulses. Analyzing the ring-down pulses can include determining a change as a function of time of a gas under measurement. The step of determining the change can have a temporal resolution of greater than 100 microseconds, greater than 10 microseconds, and/or greater than 1 microsecond.

In some embodiments, the step of analyzing the ring-down pulses can include simultaneously determining a presence of two or more species within a gas.

BRIEF DESCRIPTION OF THE DRAWINGS

The following drawings form part of the present specification and are included to further demonstrate certain aspects of systems and methods described herein, which may be better understood by reference to one or more of these drawings in combination with the detailed description of specific embodiments presented herein.

DETAILED DESCRIPTION

Figure 1:
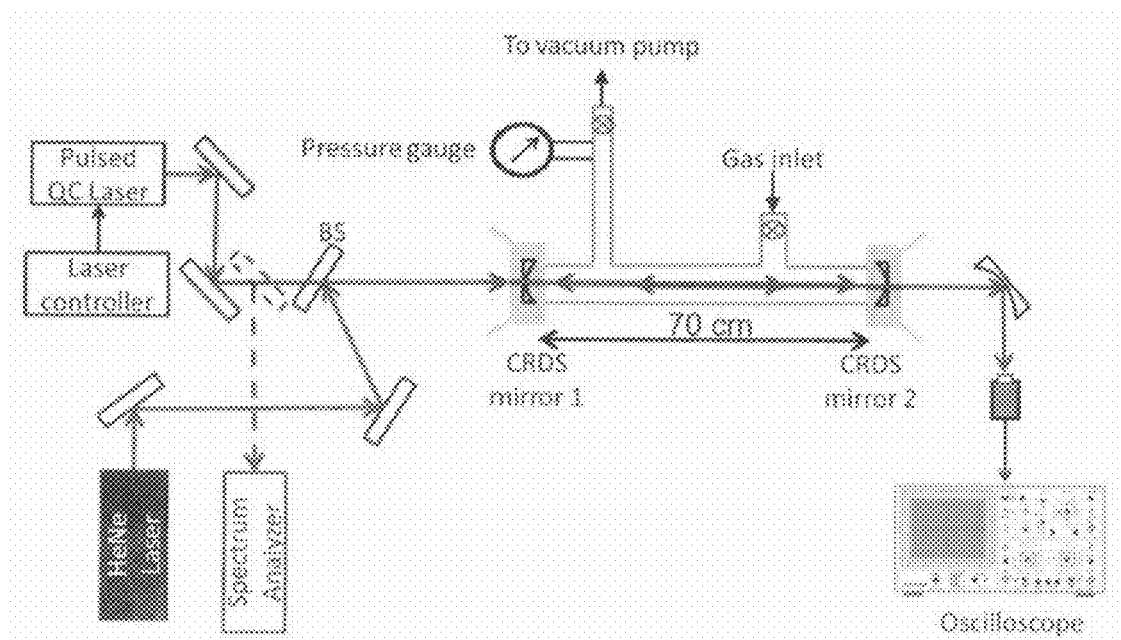
FIG. 1 depicts an exemplary cavity ring-down system embodiment.

Exemplary embodiments described, shown, and/or disclosed herein are not intended to limit the claims, but rather, are intended to instruct one of ordinary skill in the art as to various aspects of the invention. Other embodiments can be practiced and/or implemented without departing from the scope and spirit of the claimed invention.

A system for cavity ring-down spectroscopy (CRDS) can generally include a cavity that reflects light within the cavity to provide a long beam path through a sample. The decay of light intensity from the cavity over time is indicative of absorbance by the sample, and the long beam path can increase sensitivity of the system and thereby enhance the detectability of trace species within the ring-down cavity. Some of the advantages of present embodiments can include high sensitivity, high temporal resolution, wideband operating ranges, and operating ranges that can include, among others, the mid-infrared region.

CRDS can be used for sensitive detection of gas phase atomic and molecular absorptions and to achieve highly sensitive measurements of species in trace concentrations and has many applications. Some exemplary applications of CRDS can include non-invasive medical diagnosis, dangerous material detection, environmental pollution monitoring, and gas sensing for various species across industrial and governmental sectors. The system can be used to determine the strength of absorption of a sample. Detection of composition and/or concentration of species can be obtained by measuring ring-down time of a sample having a known absorption cross-section for the operating wavelength.

For further example, CRDS can be used to detect ammonia in exhaled-breath measurements with a pulsed quantum cascade laser (QCL). In one such example, a pulsed QCL at 967.35 cm$^{-1}$ has achieved sensitivity of 50 ppb for ammonia in breath with a 20-second time resolution.

Embodiments of the present ring-down spectrometer and method can provide several advantages such as, for example, sub-second measurement rates. Embodiments can also rapidly measure multiple species. Another advantage of present embodiments includes increased temporal resolution. For example, the exponential decay can be at least as short as 300 ns. Present embodiments also have wide applicability and can be useful for detecting trace gases and atmospheric pollutants, for medical diagnosis and evaluation based on respiration, for early warning systems and/or detection of dangerous, noxious, toxic, explosive, and/or biohazardous chemicals and agents. Some specific, applicable industries can include fertilizer industries, refrigeration industries, as well as applied research.

The ability of present embodiments to carry out sensitive measurements with high time resolution has applications in improving the understanding of unsteady systems such as, for example, internal combustion engines, detonation engines, shock tubes, power plants, and gas turbines, as well as many other hostile and/or dynamic environments. The advancement in laser technology over the past few decades has helped immensely in developing accurate and reliable sensors for trace gas detection. Present embodiments can take advantage of such advancements to implement a laser-based sensor which can fulfill demands of the aforementioned applications. The sensor can use a widely tunable external cavity quantum cascade laser which can enable wide wavelength coverage from 10 to 11.11 μm (1000-900 cm$^{-1}$). With some embodiments measurements of 100 ppb of ethylene with a time resolution of 0.4 s are readily achievable. In certain embodiments, the pulsed laser can have a repetition frequency as high as 100 kHz and can thus enable time resolution of 10 μs. The wide wavelength coverage of the sensor can enable detection of important trace species like ammonia, acrylonitrile, acrolein, carbonyl fluoride, ethylene, and others.

Cavity ring-down spectroscopy is a sensitive detection technique that can be realized with pulsed or continuous lasers. Current embodiments can offer better spatial resolution than direct absorption measurements performed using a multi-pass cell. Moreover, the absorption measurements performed can be immune to laser intensity fluctuations. In CRDS, light from a laser source can enter a stable optical cavity and undergo multiple passes. When the laser pulse ends, the light inside the cavity undergoes an exponential decay whose rate depends on the length of the cavity, the reflectivity of the mirrors forming the cavity and absorption losses inside the cavity. The decay time constant, also called the ring-down time, is the time taken for the light intensity to fall to 1/e of its initial value and is given as:

$$\tau = \frac{L}{c[(1-R)+\alpha d]} \qquad (1)$$

In the absence of any absorbing molecules inside the cavity, the ring-down time can be given as:

$$\tau_0 = \frac{L}{c[(1-R)]} \qquad (2)$$

In the above equations, L is the total length of the cavity, c is the speed of light, R is the reflectivity of the mirrors forming the cavity, a is the absorption coefficient in cm$^{-1}$ and d is the length of the cavity that contains absorbing molecules. By measuring the decay time constants in the presence and absence of absorbing species, the absorption coefficient can be calculated from equations (1) and (2) as:

$$\alpha = \frac{L}{cd}\left(\frac{1}{\tau}-\frac{1}{\tau_0}\right) \qquad (3)$$

The absorption coefficient α is a function of the total pressure of the gas, P, the mole fraction of the absorbing species, X, linestrength, S, and lineshape, $\phi_v$.

$$\alpha = S(T)PX\phi_v(P,T) \qquad (4)$$

The above equation (4) can enable the determination of the mole fraction of the absorbing species if other parameters (temperature and pressure) are known.

An exemplary configuration is shown in FIG. 1. The system can include a pulsed external cavity quantum cascade laser. The laser can be tunable over, for example, 9.53-12.95 μm (775-1020 cm$^{-1}$). The laser can have a repetition rate of at least 100 kHz. The laser head temperature and the wavelength on the laser controller can be adjusted. In an embodiment, the temperature and wavelength can be adjusted to get a single mode emission at the wavelength of interest. The pulsed IR laser beam emerging from the laser head can be directed into the optical cavity formed by two plano-concave mirrors. The mirrors can have, for example, a 1 m radius of curvature and/or 1" diameter, and their reflectivity can be 99.5% at 10.6 μm. The cavity mirrors can be placed several centimeters or a few meters apart. In an exemplary embodiment, the mirrors can be 70 cm apart to form a stable optical cavity configuration. The infrared laser beam leaking out of the optical cavity can be focused on a photodetector, such as a thermoelectrically cooled, optically immersed photovoltaic. In a preferred embodiment, a high bandwidth (e.g. 500 MHz) detector can be used to capture low ring-down times, which often range from 200-400 ns depending on the wavelength of operation. The detector signal can be recorded with an oscilloscope.

It should also be appreciated that while FIG. 1 depicts a linear ring-down cavity, having a first partially reflective mirror and a second partially reflective mirror, embodiments can be implemented with alternative cavities. For example, the cavity can be implemented with a triangular beam path. In such embodiments, one or two totally-reflecting mirrors can be utilized with two or one, respectively, partially-reflecting mirrors.

Various other, optional, elements are depicted in the embodiment of FIG. 1. For example, a spectrum analyzer can be incorporated to monitor laser pulses, for example, to maintain single mode emission from the laser. The information can be used to control and/or adjust the laser head controller, the laser head temperature, and/or the laser wavelength of the laser. For further example, a visible-light alignment laser can be used to aid in configuring the ring-down system when the laser head is configured to produce invisible light. A typical off-the-shelf laser useful for aligning the elements, such as the depicted 10 mW He—Ne laser, is the Thorlabs model HNL100L-EC.

Although not intending to limit the scope of the invention, but inform persons having ordinary skill in this art how to practice a single exemplary embodiment, several components commercially available can be adapted for use. For example, a system can incorporate a QCL from Daylight Solutions such as the ECqc1, model 11100-UT. The 721 Series laser spectrum analyzer from Bristol Instruments can be incorporated as a spectrum analyzer. A Vigo System IR detector (such as PVI-4TE-10.6-1x1-TO8-BaF2) can be incorporated as well. An oscilloscope, such as Tektronix DPO 3014, which has a bandwidth of 100 MHz and sampling rate of 2.5 GS/s, can be obtained and used. These commercial products, however, are not required and their specifications do not limit the elements that can be utilized. For example, the oscilloscope need not be a Tektronix scope. It need not even be digital. Embodiments can be achieved with an analog oscilloscope.

In an exemplary embodiment, a gas cell with a mirror at each of two opposing ends can define a ring-down cavity. The gas cell can be connected to a cylinder of gas to be measured. The cell can also be connected to two calibrated pressure transducers and a vacuum pump. An example of a pressure transducer is the 627D Baratron capacitance manometers from MKS Instruments, with 1000 and 10,000 Torr full scale pressure range and accuracy of 0.12%.

Figure 2:
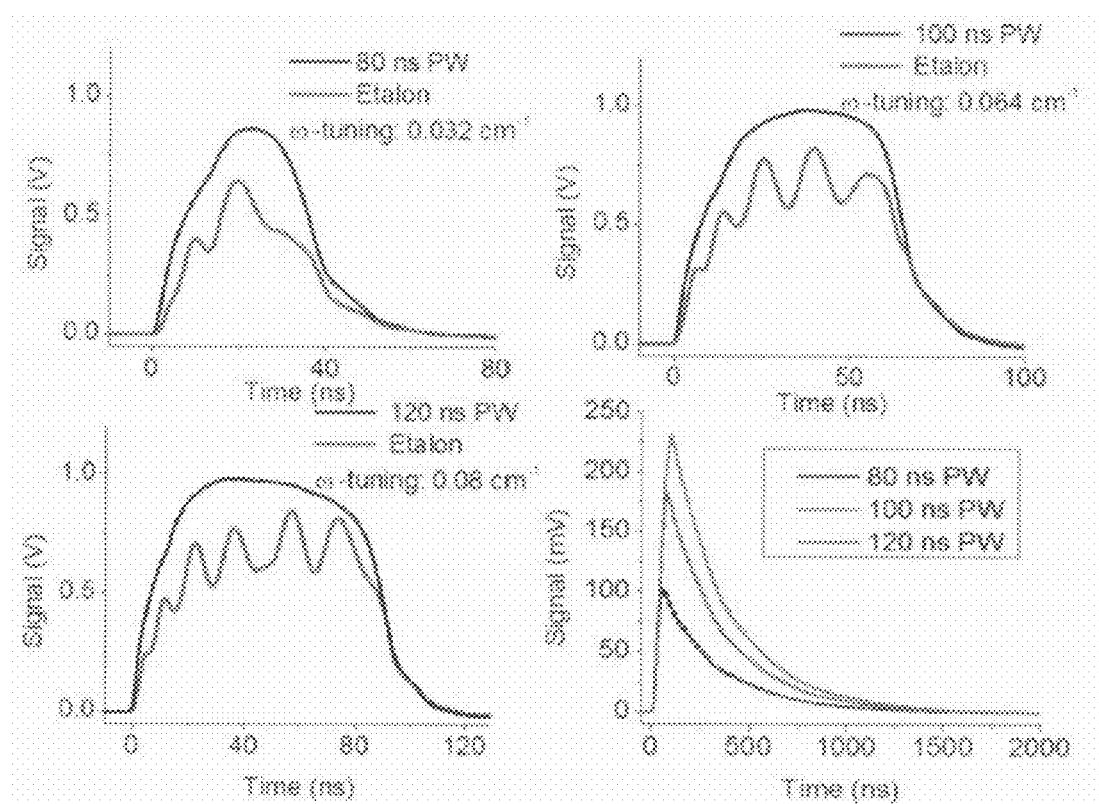
FIG. 2 depicts detected signals for different laser pulse widths.

In order to make the best use of the energy available from the pulsed laser, the laser pulse width can be varied to identify an optimum value. The frequency chirp of the laser at each pulse width can be determined by passing the laser beam through a Fabry-Perot etalon. The etalon can be a germanium etalon, for example, 76 mm long with a free spectral range of 0.016 $cm^{-1}$. The transmitted beam can be detected using a high bandwidth photovoltaic detector. The detector signal in the presence and absence of etalon can be stored for multiple pulse widths. FIG. 2 shows three different stored laser pulse widths of 80 ns, 100 ns, and 120 ns.

FIG. 2 shows that the wavelength tuning or the frequency chirp of the laser increases with increase in pulse width which can be an undesired effect because can it lead to artificial broadening of spectral features. However, increase in pulse width also increases the amount of energy entering the optical cavity thereby increasing the signal to noise ratio of the detector signal. Therefore, in an exemplary embodiment, a laser pulse width of 100 ns was selected which offers comparatively lower frequency chirp with good signal to noise ratio. All the subsequent measurements shown use a 100 ns laser pulse width.

An exemplary procedure for the alignment of the optical cavity is described. First, it is ensured that the laser beam passes through the center of all the optics which lie on the path of the beam from the laser head to the detector. This task can be accomplished with the help of the visible He—Ne laser beam which can be configured to be collinear with the infrared laser beam. Next, the mirror mounts along with the optical cell can be fixed at desired location and adjusted to ensure that the laser beam passes through their centers. A ring-down mirror can be placed on the detector side mirror mount and adjusted to ensure that the laser beam retraces its path back into the infrared laser head. The second ring-down mirror can be placed in the second mirror mount and adjusted to ensure that the back reflection goes back into the laser head. The preceding steps are sufficient to achieve a decay curve that can be seen on the oscilloscope. The alignment of the second ring-down mirror can be fine-tuned to maximize the signal on the oscilloscope to complete the alignment procedure.

An exemplary procedure for determining a mole fraction of an absorbing species inside the gas cell is described. First, the cell can be evacuated using the pump to high vacuum and then filled with non-absorbing gas (e.g. nitrogen) to a preferred pressure. Second, the laser can be switched on and a desired output wavelength can be selected on the laser controller, followed by adjustments of laser head temperature to obtain single mode emission of the desired wavelength. Single mode emission of the desired wavelength can be ensured by checking the laser spectrum on the spectrum analyzer software. However, this could be accomplished through prior calibration or other means. The signal on the detector can be recorded with the oscilloscope or with a computer. The signal can be averaged over a preferred number of pulses, for example 512 pulses. Finally, the cell can be evacuated again to high vacuum and then filled with absorbing gas to the preferred pressure. The signal on the detector can be recorded and averaged over a preferred number, for example over 512 pulses.

Figure 3:
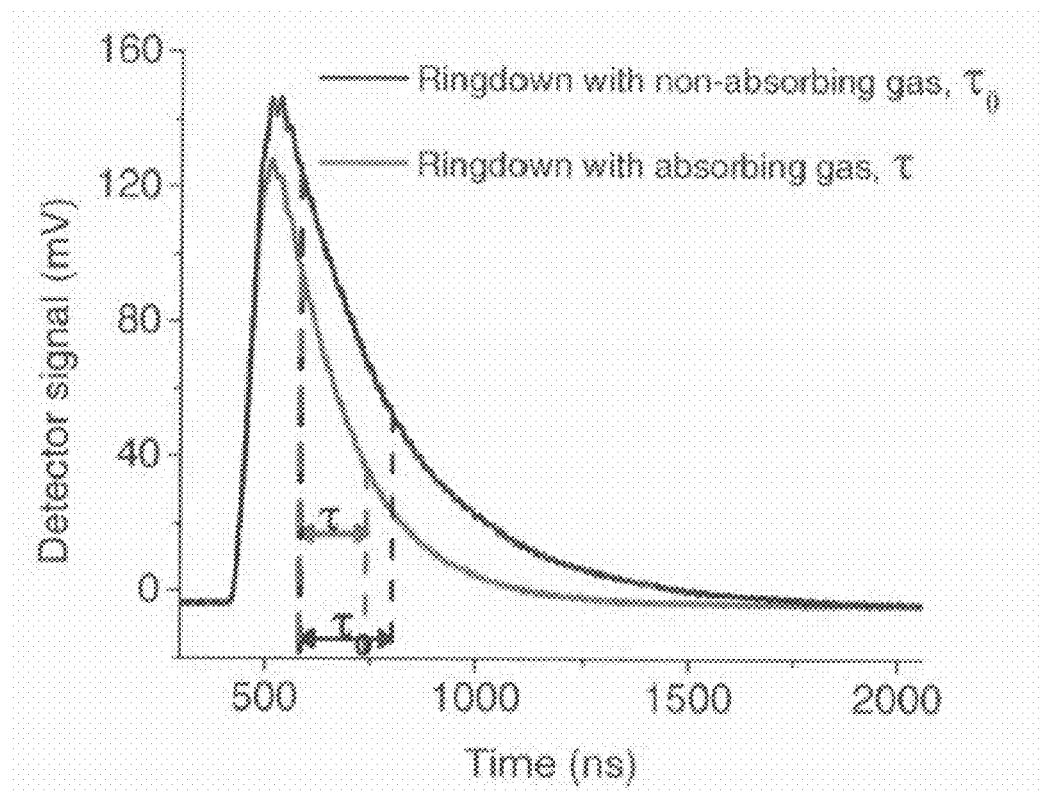
FIG. 3 depicts detected signals that have been averaged.

FIG. 3 shows the detector signal after averaging for the two cases, i.e. when a non-absorbing gas (nitrogen) is present in the cell and when the cell is filled with an absorbing gas. The ring-down times for both the cases can be determined by fitting decay curves, such as those shown in FIG. 3, with an exponential function. The absorption coefficient can then be calculated using Eqn. (3). With knowledge of the temperature and pressure inside the cell, the mole fraction of the absorbing species can be determined from the absorption coefficient by comparing it with a spectroscopic database.

Although the preceding techniques are described in specific orders, the described order is not necessarily required and can be modified without departing from the spirit and scope of the invention as claimed.

The CRDS system herein is very flexible and can be tailored to suit diverse applications with little or no change in the hardware. While on one hand, the sensor can be used for making highly sensitive measurements of species concentrations with sub-second time resolution, it can at the same time be utilized for making highly time-resolved measurements. This incredible flexibility of the sensor makes it a suitable candidate for a wide range of applications, some of which have been described herein. The wide operating range of the sensor can enable measurement of numerous species in trace concentrations namely ammonia, acrylonitrile, ethylene and others.

Ammonia detection at trace concentrations is hugely important for a number of applications. Elevated levels of ammonia (>1 ppm) in exhaled breath have been linked to a variety of adverse medical conditions like Chronic Kidney Disease (CKD). Quantitative measurement of ammonia levels in exhaled breath can be used as an indicator of kidney malfunction and also for determining the time needed for the required degree of dialysis. Ammonia concentration measurements is a significant part of environmental gas analysis especially near farming sites where high concentration levels of ammonia can be a serious health threat. Moreover, detection of trace levels of ammonia in motor vehicle exhaust and industrial emissions is vital for air quality control. In the fertilizer factories, chemical industry and refrigeration systems which make use of almost pure ammonia, any leakage of ammonia in the system can cause life-threatening situations. All such facilities should have ammonia gas sensors connected to alarm systems so as to warn in case of ammonia reaching dangerously high concentrations. The U.S. Occupational Safety and Health Administration (OSHA) has set an 8-hour exposure limit for ammonia of 25 ppm by volume in environmental air.

Detection of acrylonitrile at trace levels is also important as it has been classified as a major air pollutant due to its adverse health and environmental effects. Adverse health effects include allergic, respiratory and cardiovascular distresses. Apart from air quality control, industrial gas sensors for detecting acrylonitrile in the workspace environment are equally important to avoid adverse health effects mentioned above. The maximum allowed workspace acrylonitrile level is 2 ppm as set by OSHA. Acrylonitrile is used in the production of plastics and synthetic fibers.

Ethylene detection at trace levels is important in applications such as air quality control, plant biology and combustion. Industrial emissions, waste incineration plants and vehicle exhaust fumes are the major sources of ethylene in the atmosphere. As a volatile organic compound, ethylene can be involved in reactions producing ozone which can damage crops and materials. Ethylene is also a pivotal hormone in plant biology, thereby making its detection important in controlling fruit ripening process. Ethylene concentrations range between 1 to 10 ppm for fruit ripening control.

The ability of embodiments to provide highly time-resolved measurements can provide several advantages in various applications. For example, sensitive CRDS measurements can be stored and time histories of species in unsteady systems can be analyzed, such as internal combustion engines, gas turbines, and shock tubes. Ethylene is an important intermediate species in combustion and is formed primarily during the oxidation and pyrolysis of larger alkanes. It is one of the primary species involved in the formation of benzene which is a precursor of soot. Ethylene, due to its high temperature stability, is a dominant intermediate during alkane pyrolysis and oxidation which can make the measurement of time-resolved ethylene concentration data advantageous.

Embodiments can be characterized by exemplary implementations such as measurements of trace concentrations of ethylene in laboratory air and in air samples in a car parking facility. The fast response performance time can also be demonstrated by an implementation for measuring a known concentration of carbon dioxide at different time resolutions.

Carbon dioxide as a test molecule can be useful because its spectroscopy is very well known. Simulations based on HITRAN database can be performed to identify the wavelengths at which measurements of carbon dioxide could be carried out while considering the limitations imposed by the wavelength-dependent mirror reflectivity. As trace concentration of ethylene maybe present in nitrogen as an impurity and since ethylene has a very strong transition centered at 949.36 $cm^{-1}$, simulations can be performed to identify the strong absorption lines of carbon dioxide where the interference from ethylene would be minimal.

Figure 4:
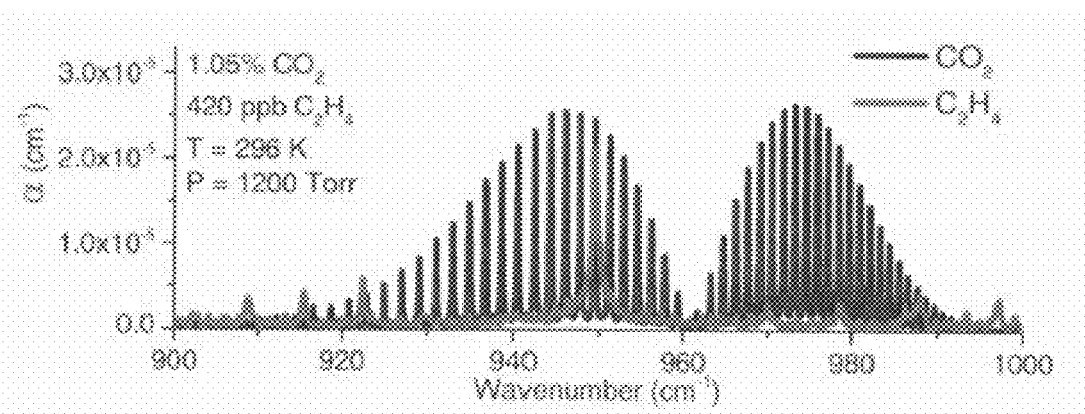
FIG. 4 depicts absorption lines for $CO_2$ and for $C_2H_4$.

FIG. 4 shows the absorption coefficient for a mixture of 1.05% carbon dioxide and 420 ppb of ethylene over the range 900-1000 $cm^{-1}$. The absorption lines of carbon dioxide centered at 938.688 $cm^{-1}$ and at 974.6219 $cm^{-1}$ are of interest in the exemplary method due to minimal interference from ethylene and to demonstrate part of the wide tuning range of this sensor.

Figure 5:
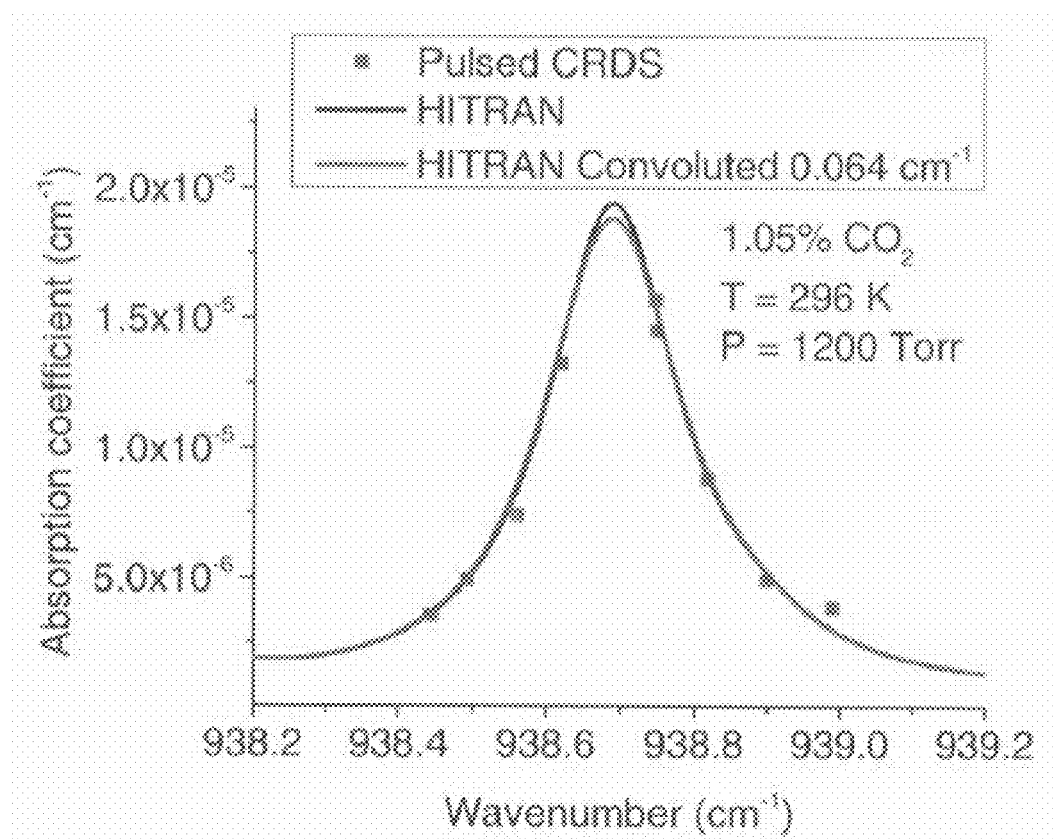
FIG. 5 depicts a comparison of a measured absorption and simulated data.
Figure 6:
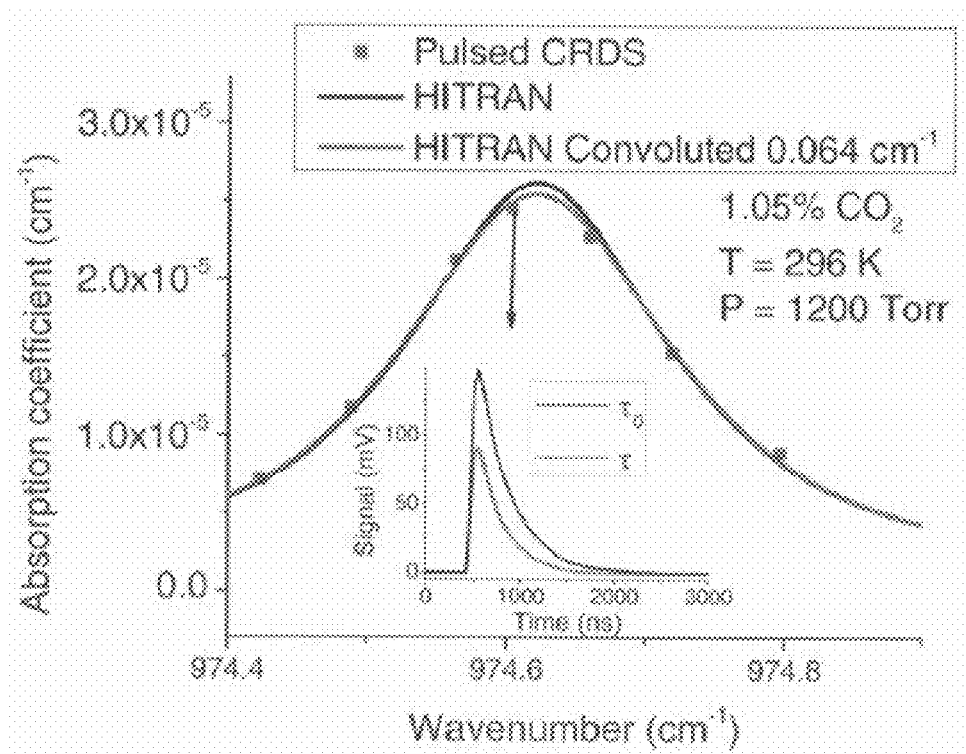
FIG. 6 depicts a comparison of a measured absorption and simulated data.

Measurements here are based on a laser pulse width of 100 ns. With a view to minimize the effect of artificial broadening due to the frequency chirp of the laser at 100 ns pulse widths, the absorption measurements of carbon dioxide mixture can be performed at a relatively high pressure of 1200 Torr. FIGS. 5 and 6 show a comparison between simulated absorption coefficients and measured absorption coefficient for absorption lines centered at 938.688 $cm^{-1}$ and 974.6219 $cm^{-1}$, respectively. The black line represents a simulated absorption coefficient obtained without considering effects of laser frequency chirp. The gray line represents an absorption coefficient obtained by convoluting the simulated absorption coefficient with a top hat profile of 0.064 $cm^{-1}$ width which corresponds to the frequency chirp of 100 ns laser pulse width. It can be seen from the figures that the measured absorption coefficient agrees well with the convoluted absorption coefficient at both wavelengths.

The standard deviation in the measured ring-down time for all measurements can be less than about 3 ns. The minimum detectable absorption coefficient can be calculated as:

$$\alpha_{min} = \frac{1}{c\tau_0}\left(\frac{\sigma}{\tau_0}\right) \quad (5)$$

where $\sigma$ is the standard deviation in the ring down time, c is the speed of light and $\tau_o$ is the ring-down time in a cell filled with nitrogen at 760 Torr. As seen from Eqn. (5), the minimum detectable absorption coefficient can depend on the ring down time and therefore on the laser wavelength under consideration.

Table 1 shows ring down times measured at different wavelengths and corresponding minimum absorption coefficients.

TABLE 1

Minimum detectable absorption coefficient for different laser wavelengths

| Frequency ($cm^{-1}$) | Empty ring down time (ns) | Standard deviation in RDT (ns) | Minimum absorption coefficient ($cm^{-1}$) |
|---|---|---|---|
| 898.47 | 239.73 | 3 | $1.74 \times 10^{-6}$ |
| 949.475 | 259.34 | 3 | $1.49 \times 10^{-6}$ |
| 1001.243 | 227.05 | 3 | $1.94 \times 10^{-6}$ |

The minimum detectable absorption coefficient over the frequency range 900-1000 $cm^{-1}$ is less than $2 \times 10^{-6}$ $cm^{-1}$. Therefore, using $2 \times 10^{-6}$ $cm^{-1}$ as the minimum detectable absorption coefficient for the sensor, the detection limits for species that absorb in the operating range of the sensor can be predicted and are presented in Table 2. To predict the detection limits for all the molecules listed in Table 2, a pressure of 760 Torr and temperature of 298 K is assumed.

The high sensitivity and the wide operating range of the sensor can achieve sub-ppm level detection of five molecules. Moreover, the detection limits for three molecules namely ammonia, acrylonitrile and carbonyl fluoride are much lower than the maximum exposure limits recommended by OSHA. Therefore, present embodiments can be suitable for industrial applications which need to constantly monitor the concentrations of these molecules.

TABLE 2

Predicted detection limit of molecules

| Species | Frequency (cm$^{-1}$) | Detection limit (ppb) | Recommended maximum exposure limit (ppb) |
|---|---|---|---|
| Ammonia | 967.371 | 41 | 25000 |
| Acrylonitrile | 953.626 | 128 | 2000 |
| Carbonyl fluoride | 973.7 | 288 | 2000 |
| Acrolein | 958.7536 | 159 | 100 |
| Ethylene | 949.475 | 52 | — |

Exemplary Method Using Ethylene ($C_2H_4$)

The capability of the sensor to measure molecules in trace concentrations can be demonstrated by measuring trace concentrations of ethylene. The Pacific Northwest National Laboratory (PNNL) quantitative IR database can be used for comparison with the measured absorption coefficients as it is a reliable source for the spectral transitions of ethylene near 949 cm$^{-1}$. Ethylene measurements can be performed at 949.475 cm$^{-1}$ and at nominal temperature of 296 K and pressure of 760 Torr.

Figure 7:
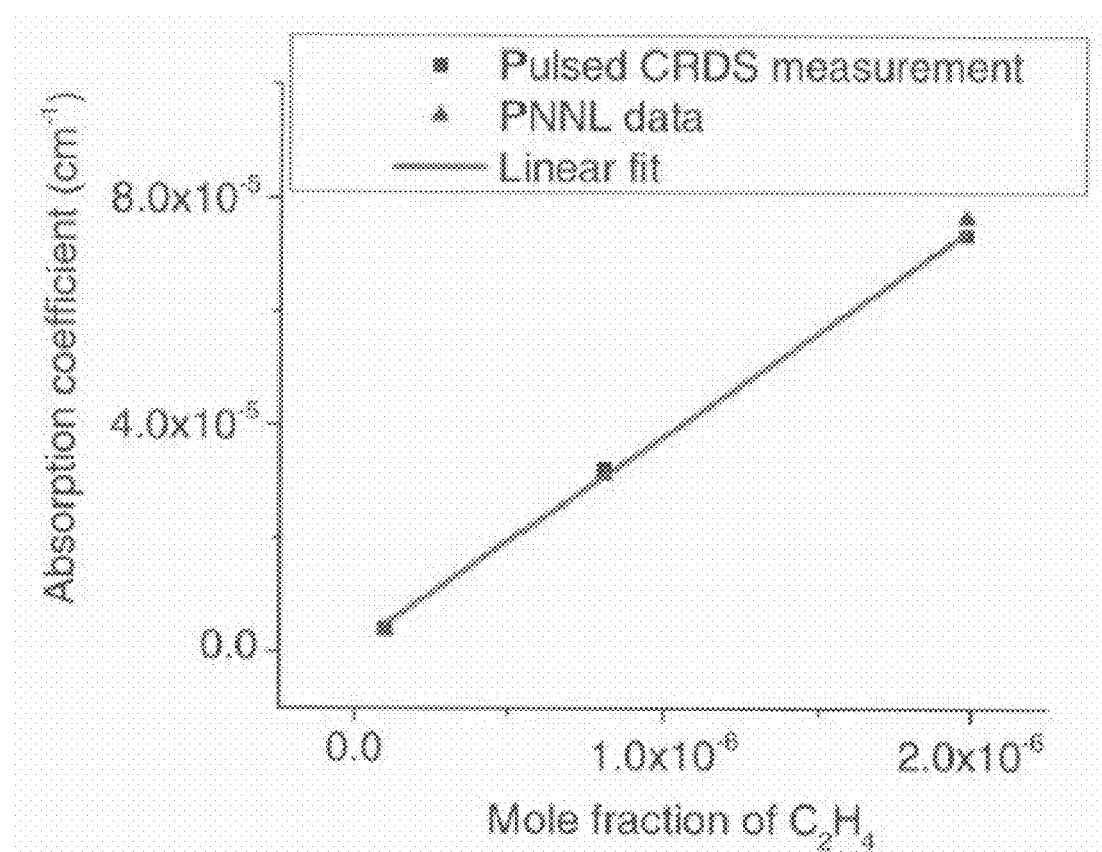
FIG. 7 depicts absorption coefficient as a function of mole fraction.

FIG. 7 shows absorption coefficients for three different mole fractions of ethylene. The largest mole fraction shown is 2.35 ppm, the smallest being 100 ppb of ethylene. Empirical absorption coefficients agreed well with PNNL database with a maximum deviation of about 4%.

Due to significant interference from carbon dioxide at 949.475 cm$^{-1}$, the absorption coefficient from air in the parking facility can be performed at 949.835 cm$^{-1}$. In laboratory air, the concentration of ethylene can be about 55 ppb, which is close to the expected value for indoor clean air. The sample collected from the automobile garage showed the concentration of ethylene to be about 415 ppb. Compared to laboratory air, the elevated levels of ethylene found in the air sample collected at the automobile parking lot could be attributed to vehicular pollution.

The above exemplary implementations using ethylene demonstrate capabilities of embodiments to measure trace concentrations of molecules in the atmosphere.

Figure 8:
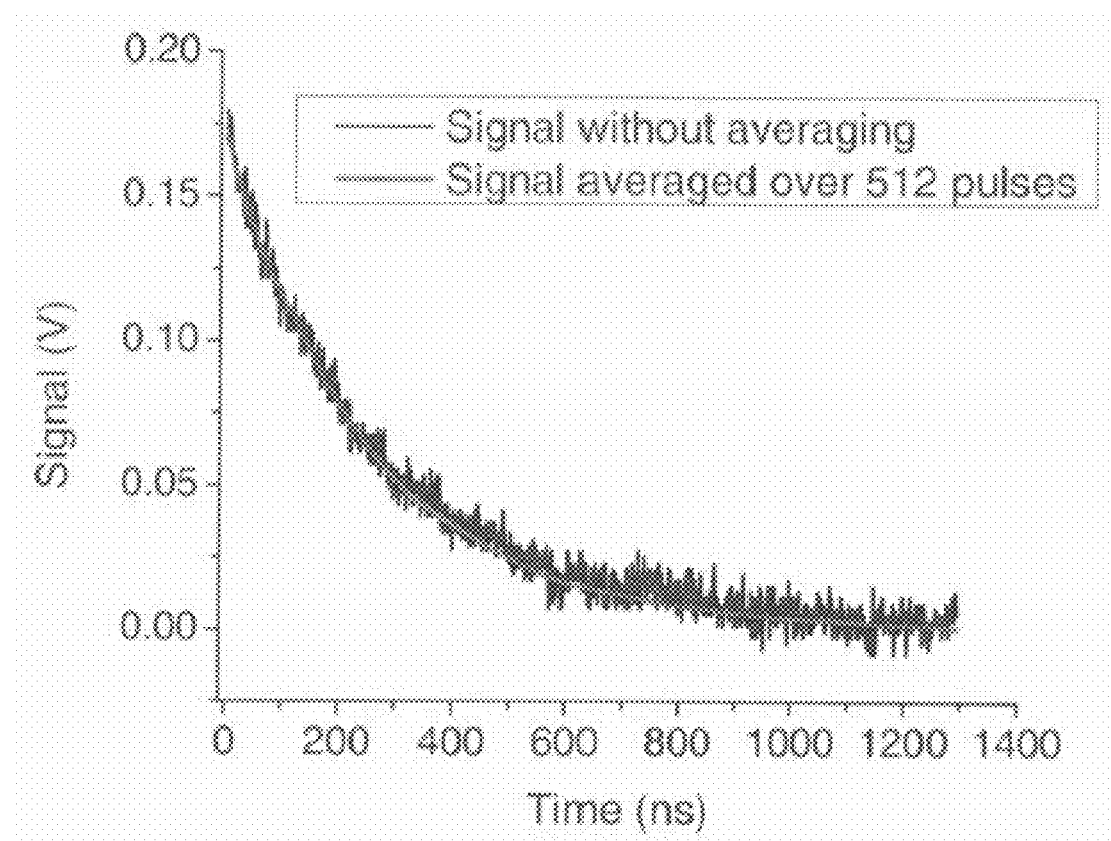
FIG. 8 depicts a raw signal and an averaged signal.

FIG. 8 shows a detector signal without averaging in comparison with a detector signal averaged over 512 pulses. Noise in the detector signal can significantly decrease after averaging thereby increasing the sensitivity of the sensor.

The averaged signal can be fitted using an exponential function to extract ring-down times. Shown are eighty successive ring-down times averaged to calculate the absorption coefficient. Post-processing can lead to an averaging time of 0.4 s.

Figure 9:
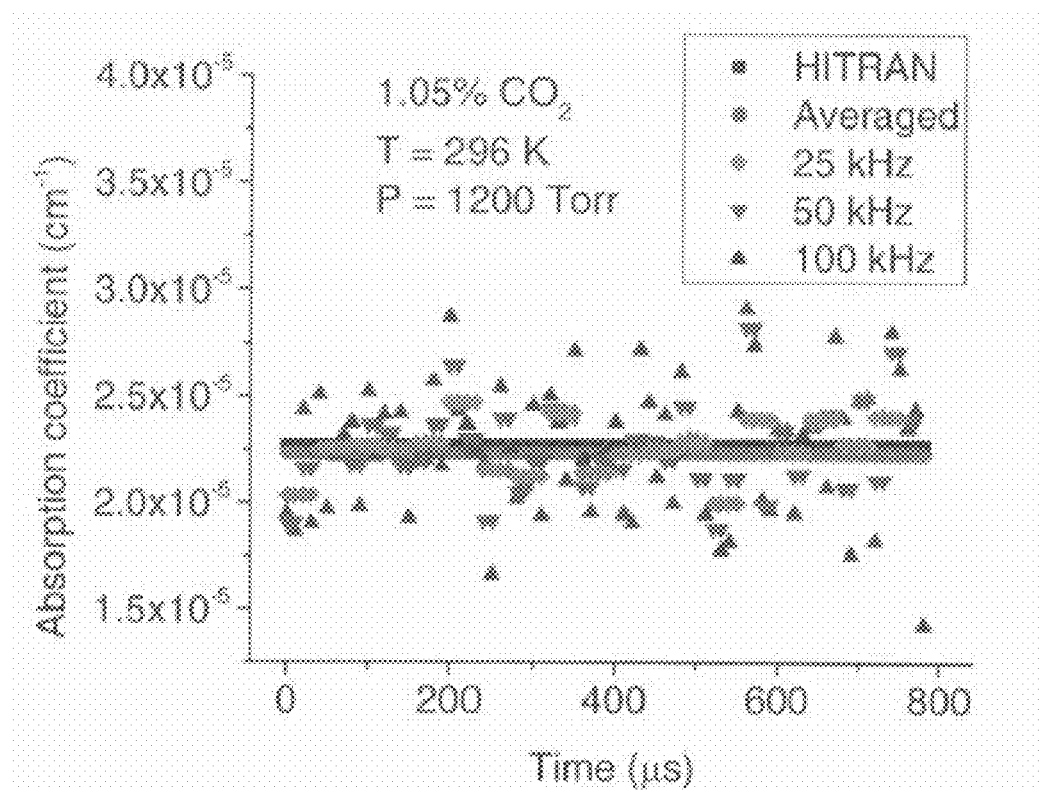
FIG. 9 depicts an absorption coefficient for $CO_2$ for different time resolutions.

The effect of time resolution on the absorption coefficient can be determined, for example, to exploit the potential of this sensor for fast time response measurements. FIG. 9 shows an absorption coefficient measured at different time resolutions for a mixture of 1.05% carbon dioxide in nitrogen. The noise in the absorption coefficient can decrease with an increase in the averaging time and the noise can be quite low for the case with averaging time of 0.4 seconds, denoted in FIG. 9 by the legend symbol "Averaged". The noise in absorption coefficient is higher for the case with the best time resolution of 10 μs, which is denoted by the legend symbol "100 kHz" in FIG. 9. The time resolution of 10 μs can be obtained by, for example, determining the ring-down time without averaging the detector signal. For lower time resolutions of 20 μs and 40 μs the detector signal can be fitted to extract the ring-down time. The decay times obtained can then be averaged over successive pulses. In the exemplary method, they were averaged over 2 successive pulses and 4 successive pulses, respectively. This particular exemplary method of fitting the detector signal first and then averaging the ring-down times can reduce the noise in the absorption coefficient as compared to averaging the detector signal first and then fitting the averaged signal later.

Table 3 shows the noise for different averaging times. For a 10 μs time resolution, the noise in the absorbance can be approximately 0.1% and the noise can decrease to about 0.034% for a 40 μs time resolution. The absorbance noise at 10 μs time resolution is good enough for this sensor to be used for performing sensitive measurements in unsteady systems like engines and shock tubes. The sensitivity can be further improved by using higher reflectivity mirrors. It is to be noted that the time resolution of 10 μs is limited merely by the 100 kHz repetition rate of the pulsed laser used in this exemplary embodiment and is not affected by the use of higher reflectivity mirrors.

TABLE 3

Absorbance noise for different time resolutions

| Data | $\tau_{mean}$(ns) | $\tau_{min}$(ns) | $\tau_{max}$(ns) | $\tau_o$(ns) | $\alpha_{vmin}$(cm$^{-1}$) | $\alpha_{vmax}$(cm$^{-1}$) | $\alpha_{vmean}$(cm$^{-1}$) | Absorbance noise (%) |
|---|---|---|---|---|---|---|---|---|
| HITRAN | 258.99 | 258.99 | 258.99 | 314.44 | 2.27 × 10$^{-5}$ | 2.27 × 10$^{-5}$ | 2.27 × 10$^{-5}$ | 0 |
| Average | 259.77 | 259.77 | 259.77 | 314.44 | 2.23 × 10$^{-5}$ | 2.23 × 10$^{-5}$ | 2.23 × 10$^{-5}$ | 0 |
| 25 kHz | 259.23 | 255 | 264.59 | 314.44 | 2.47 × 10$^{-5}$ | 1.99 × 10$^{-5}$ | 2.26 × 10$^{-5}$ | 0.034 |
| 50 kHz | 259.23 | 248.3 | 267.06 | 314.44 | 2.82 × 10$^{-5}$ | 1.88 × 10$^{-5}$ | 2.26 × 10$^{-5}$ | 0.066 |
| 100 kHz | 259.23 | 246.7 | 277.17 | 314.44 | 2.91 × 10$^{-5}$ | 1.42 × 10$^{-5}$ | 2.26 × 10$^{-5}$ | 0.1 |

Embodiments can be implemented as portable systems for use in the field. For example, embodiments can be implemented with pre-calibrated and/or aligned components disposed in a durable and/or portable housing for use by environmental monitoring agencies, industries, healthcare facilities, security checkpoints, and/or research labs.

Further refinements of some embodiments can include improving the sensitivity of the sensor by utilizing higher reflectivity mirrors. On the other hand, an advantage of some implementations of the CRDS system includes the ability to use a relatively low-power quantum cascade laser afforded by low reflectivity mirrors of the resonating cavity. This advantage can allow compact, lightweight configurations.

The portability, sensitivity, non-intrusiveness, accuracy, and high time resolution capability makes present embodiments particularly useful from a process control and/or a diagnostic tool perspective. Utilizing, for example, a pulsed external cavity quantum cascade lasers in the CRDS system can provide additional advantages. For example, the wide tuning range of external cavity quantum cascade laser coupled with the relatively wide reflectivity curve of the mirrors can lead to wide operating ranges of over a 900-1000 $cm^{-1}$ wavenumber region. This can allow detection of a plurality of trace gases using a single sensor. Further, a kilohertz repetition rate provides highly time-resolved measurements with a response time of the order of microseconds. The ability of the sensor to measure multiple species in trace concentrations can be an enormous advantage when compared to prior sensors, which can measure no more than two molecules because of narrower operating ranges.

The embodiments may take the form of a hardware embodiment, a software embodiment, or an embodiment combining software and hardware. In one embodiment, the present invention takes the form of a computer-program product that includes computer-useable instructions embodied on one or more computer-readable media.

The various integrated techniques, methods, and systems described herein can be implemented in part or in whole using computer-based systems and methods. Additionally, computer-based systems and methods can be used to augment or enhance the functionality described herein, increase the speed at which the functions can be performed, and provide additional features and aspects as a part of or in addition to those described elsewhere in this document. Various computer-based systems, methods and implementations in accordance with the described technology are presented below.

Embodiments may include a general-purpose computer and can have an internal or external memory for storing data and programs such as an operating system (e.g., DOS, Windows 2000™, Windows XP™, Windows NT™, OS/2, UNIX or Linux) and one or more application programs. Examples of application programs include computer programs implementing the techniques described herein for lyric and multimedia customization, authoring applications (e.g., word processing programs, database programs, spreadsheet programs, or graphics programs) capable of generating documents or other electronic content; client applications (e.g., an Internet Service Provider (ISP) client, an e-mail client, or an instant messaging (IM) client) capable of communicating with other computer users, accessing various computer resources, and viewing, creating, or otherwise manipulating electronic content; and browser applications (e.g., Microsoft's Internet Explorer) capable of rendering standard Internet content and other content formatted according to standard protocols such as the Hypertext Transfer Protocol (HTTP). One or more of the application programs can be installed on the internal or external storage of the general-purpose computer. Alternatively, in another embodiment, application programs can be externally stored in or performed by one or more device(s) external to the general-purpose computer.

The general-purpose computer may include a central processing unit (CPU) for executing instructions in response to commands, and a communication device for sending and receiving data. One example of the communication device is a modem. Other examples include a transceiver, a communication card, an antenna, a network adapter, or some other mechanism capable of transmitting and receiving data over a communications link through a wired or wireless data pathway.

The general-purpose computer may also include an input/output interface that enables wired or wireless connection to various peripheral devices. Examples of peripheral devices include, but are not limited to, a mouse, a mobile phone, a personal digital assistant (PDA), a keyboard, a display monitor with or without a touch screen input, and an audiovisual input device. In another implementation, the peripheral devices may themselves include the functionality of the general-purpose computer. For example, the mobile phone or the PDA may include computing and networking capabilities and function as a general purpose computer by accessing a network and communicating with other computer systems. Examples of a network that can be utilized to implement various embodiments include the Internet, the World Wide Web, WANs, LANs, analog or digital wired and wireless telephone networks (e.g., Public Switched Telephone Network (PSTN), Integrated Services Digital Network (ISDN), and Digital Subscriber Line (xDSL)), radio, television, cable, or satellite systems, and other delivery mechanisms for carrying data. A communications link can include communication pathways that enable communications through one or more networks.

In one implementation, a processor-based system of the general-purpose computer can include a main memory, preferably random access memory (RAM), and can also include a secondary memory. The secondary memory can include, for example, a hard disk drive or a removable storage drive, representing a floppy disk drive, a magnetic tape drive, an optical disk drive (Blu-Ray, DVD, CD drive), magnetic tape, paper tape, punched cards, standalone RAM disks, Iomega Zip drive, etc. The removable storage drive can read from or write to a removable storage medium. A removable storage medium can include a floppy disk, magnetic tape, optical disk (Blu-Ray disc, DVD, CD) a memory card (CompactFlash card, Secure Digital card, Memory Stick), paper data storage (punched card, punched tape), etc., which can be removed from the storage drive used to perform read and write operations. As will be appreciated, the removable storage medium can include computer software or data.

In alternative embodiments, the secondary memory can include other similar means for allowing computer programs or other instructions to be loaded into a computer system. Such means can include, for example, a removable storage unit and an interface. Examples of such can include a program cartridge and cartridge interface (such as the found in video game devices), a removable memory chip (such as an EPROM or PROM) and associated socket, and other removable storage units and interfaces, which allow software and data to be transferred from the removable storage unit to the computer system.

In one embodiment, a network can include a communications interface that allows software and data to be transferred between client devices, central servers, and other components. Examples of communications interfaces can include a modem, a network interface (such as, for example, an Ethernet card), a communications port, and a PCMCIA slot and card. Software and data transferred via a communications interface may be in the form of signals, which can be electronic, electromagnetic, optical or other signals capable of being received by a communications interface. These signals may be provided to a communications interface via a channel capable of carrying signals and can be implemented using a wireless medium, wire or cable, fiber optics or other communications medium. Some examples of a channel can include a phone line, a cellular phone link, an RF link, a network interface, and other suitable communications channels.

In this document, the terms "computer program medium" and "computer readable medium" are generally used to refer to media such as a removable storage device, a disk capable of installation in a disk drive, and signals on a channel. These computer program products may provide software or program instructions to a computer system.

Computer-readable media include both volatile and non-volatile media, removable and non-removable media, and contemplate media readable by a database, a switch, and various other network devices. Network switches, routers, and related components are conventional in nature, as are means of communicating with the same. By way of example, and not limitation, computer-readable media include computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, DVD, holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal. The term "modulated data signal" refers to a propagated signal that has one or more of its characteristics set or changed to encode information in the signal. An exemplary modulated data signal includes a carrier wave or other transport mechanism. Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

In an embodiment where the elements are implemented using software, the software can be stored in, or transmitted via, a computer program product and loaded into a computer system using, for example, a removable storage drive, hard drive or communications interface. The control logic (software), when executed by the processor, may cause the processor to perform the functions of the techniques described herein.

In another embodiment, the elements may be implemented primarily in hardware using, for example, hardware components such as PAL (Programmable Array Logic) devices, application specific integrated circuits (ASICs), or other suitable hardware components. Implementation of a hardware state machine so as to perform the functions described herein will be apparent to a person skilled in the relevant art(s). In yet another embodiment, elements may be implanted using a combination of both hardware and software.

In another embodiment, the computer-based methods can be accessed or implemented over the World Wide Web by providing access via a Web Page to the methods described herein. Accordingly, the Web Page may be identified by a Universal Resource Locator (URL). The URL may denote both a server and a particular file or page on the server.

Each of the following references is hereby incorporated by reference in its entirety.

Rao G. N., and Karpf A., 2010, "High sensitivity detection of $NO_2$ employing cavity ringdown spectroscopy and an external cavity continuously tunable quantum cascade laser," Applied optics, 49(26), pp. 4906-4914.

O'Keefe and Deacon, 1988, "Cavity ring-down optical spectrometer for absorption measurements using pulsed laser sources," Review of Scientific Instruments, 59(12), pp. 2544-551.

Berden et al., 2000, "Cavity ring-down spectroscopy: Experimental schemes and applications," International Reviews in Physical Chemistry, 19(4), pp. 565-607.

Manne et al., 2006, "Pulsed quantum cascade laser-based cavity ring-down spectroscopy for ammonia detection in breath," Applied optics, 45(36), pp. 9230-37.

Timmer et al., 2005, "Ammonia sensors and their applications—a review," Sensors and Actuators B: Chemical, 107(2), pp. 666-677.

Manne et al., 2012, "Sensitive detection of acrolein and acrylonitrile with a pulsed quantum-cascade laser," Applied Physics B: Lasers and Optics, 107(2), pp. 441-47.

Weidmann et al., 2004, "Monitoring of ethylene by a pulsed quantum cascade laser," Applied optics, 43(16), pp. 3329-334.

Pilla et al., 2011, "Shock tube/laser absorption measurements of ethylene time-histories during ethylene and n-heptane pyrolysis," Proceedings of the Combustion Institute, 33(1), pp. 333-340.

Schilt et al., 2004, "Ammonia monitoring at trace level using photoacoustic spectroscopy in industrial and environmental applications," Spectrochimica Acta Part A: Molecular and Biomolecular Spectroscopy, 60(14), pp. 3259-268.

Rothman et al., 2009, "The HITRAN 2008 molecular spectroscopic database," Journal of Quantitative Spectroscopy and Radiative Transfer, 110(9-10), pp. 533-572.

2013, "NIOSH Pocket Guide to Chemical Hazards". Available online at www.cdc.gov/niosh/npg/.

Sharpe et al., 2004, "Gas-phase databases for quantitative infrared spectroscopy," Applied spectroscopy, 58(12), pp. 1452-461.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope or the invention. In addition, from the foregoing it will be seen that this invention is one well adapted to attain all the ends and objects set forth above, together with other advantages. It will be understood that certain features and sub-combinations are of utility and may be employed without reference to other features and sub-combinations. This is contemplated and within the scope of the appended claims. All such similar substitutes and modifications apparent to those skilled in the art are deemed to be within the spirit and scope of the invention as defined by the appended claims.

What is claimed is:

1. A ring-down spectrometer, comprising:
   an external two-mirror cavity pulsed quantum cascade laser configured to produce a laser beam;
   an optical ring-down cavity, wherein the laser beam is arranged to propagate through the optical cavity;

a photo detector configured to receive the laser beam and produce signals;

a computer configured to receive the signals from the photo detector; and wherein the computer is further configured to measure ring-down time and to average the signals.

2. The ring-down spectrometer of claim 1, wherein the external cavity pulsed quantum cascade laser comprises a laser controller, and wherein the optical ring-down cavity comprises at least one mirror having a reflectivity of at least 99.5 percent.

3. The ring-down spectrometer of claim 2, further comprising a spectral analyzer.

4. The ring-down spectrometer of claim 3, wherein the laser controller is configured to tune the quantum cascade laser based on an output from the spectrum analyzer.

5. The ring-down spectrometer of claim 4, wherein the quantum cascade laser is configured to provide a single mode laser beam.

6. The ring-down spectrometer of claim 1, wherein the laser beam comprises pulses having pulse widths of less than 1 microsecond.

7. The ring-down spectrometer of claim 1, wherein the laser beam comprises pulses having pulse widths of less than 300 nanoseconds.

8. The ring-down spectrometer of claim 1, wherein the laser beam comprises pulses having pulse widths of less than 100 nanoseconds.

9. The ring-down spectrometer of claim 8, wherein the photo detector and the computer are configured to provide a temporal resolution of greater than 10 microseconds.

10. A ring-down spectroscopic method, comprising:
producing laser pulses with an external two-mirror cavity pulsed quantum cascade laser, wherein each of the pulses have a pulse width of less than 200 nanoseconds;

propagating the laser pulses through an optical ring-down cavity having at least one partially reflecting mirror to produce ring-down pulses;

detecting the ring-down pulses; and analyzing the ring-down pulses to determine an absorption coefficient based on a ring-down time.

11. The method of claim 10, wherein producing the laser pulses comprises varying the pulse width to identify an optimum value.

12. The method of claim 10, wherein the pulse width of less than 1 microsecond.

13. The method of claim 10, wherein the pulse width of less than 300 nanoseconds.

14. The method of claim 13, wherein the laser pulses have a bandwidth greater than 600 picometers.

15. The method of claim 10, wherein the pulse width of less than 100 nanoseconds.

16. The method of claim 10, wherein analyzing the ring-down pulses comprises removing noise.

17. The method of claim 16, wherein removing noise comprises averaging a plurality of the ring-down pulses.

18. The method of claim 10, wherein analyzing the ring-down pulses comprises determining a change as a function of time of a gas under measurement.

19. The method of claim 18, wherein determining the change has a temporal resolution of greater than 100 microseconds.

20. The method of claim 18, wherein determining the change has a temporal resolution of greater than 10 microseconds.

21. The method of claim 18, wherein determining the change has a temporal resolution of greater than 1 microsecond.

22. The method of claim 10, wherein analyzing the ring-down pulses comprises simultaneously determining a presence of two or more species within a gas.

* * * * *